(12) United States Patent
Locke et al.

(10) Patent No.: US 7,060,854 B2
(45) Date of Patent: Jun. 13, 2006

(54) PROCESS FOR MAKING POLYMORPHIC FORM A OF 4-[6-ACETYL-3-[3-(4-ACETYL-3-HYDROXY-2-PROPYLPHENYLTHIO)PROPOXY]-2-PROPYLPHENOXY]BUTYRIC ACID

(75) Inventors: Kenneth Walter Locke, Carlsbad, CA (US); David Gregory Roe, Rockwood (CA)

(73) Assignee: MediciNova, Inc., San Diego, CA (US)

( * ) Notice: Subject to any disclaimer, the term of this patent is extended or adjusted under 35 U.S.C. 154(b) by 0 days.

(21) Appl. No.: 10/601,861

(22) Filed: Jun. 24, 2003

(65) Prior Publication Data

US 2004/0267041 A1  Dec. 30, 2004

(51) Int. Cl.
*C07C 321/00* (2006.01)

(52) U.S. Cl. ...................................... 562/431
(58) Field of Classification Search ............... 560/9, 560/11; 562/426, 429, 431
See application file for complete search history.

(56) References Cited

U.S. PATENT DOCUMENTS 4,985,585 A  1/1991  Ohashi et al. ................. 560/9

*Primary Examiner*—Cecilia J. Tsang
*Assistant Examiner*—Taylor Victor Oh
(74) *Attorney, Agent, or Firm*—Katten Muchin Rosenman LLP; Gilberto M. Villacorta

(57) ABSTRACT

Process for making a pharmaceutical composition, comprising: a compound of formula (1) in crystalline form:

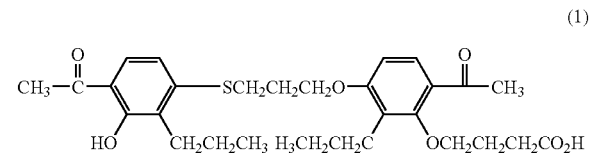

together with a pharmaceutically acceptable carrier or excipient, wherein the compound of formula (1) is present in polymorphic crystal form A substantially free of other polymorphs, and methods for making this polymorph.

9 Claims, 9 Drawing Sheets

2Θ

PROCESS FOR MAKING POLYMORPHIC FORM A OF 4-[6-ACETYL-3-[3-(4-ACETYL-3-HYDROXY-2-PROPYLPHENYLTHIO) PROPOXY]-2-PROPYLPHENOXY]BUTYRIC ACID

BACKGROUND OF THE INVENTION

1. Field of the Invention

The polymorphic form A, as defined by powder x-ray diffraction, of 4-[6-acetyl-3-[3-(4-acetyl-3-hydroxy-2-propylphenylthio)propoxy]-2-propylphenoxy]butyric acid has high solubility and bioavailability compared to other crystalline forms.

2. Description of the Background

Leukotrienes are metabolites of arachidonic acid through the 5'-lipoxygenase pathway and are important mediators of allergic response, such as that involved in bronchial asthma. Drugs that exert antagonistic effects on the leukotrienes are useful for the treatment of allergic diseases.

The synthesis and biological activity of many phenoxyalkylcarboxylic acid derivatives, which are leukotriene antagonists, are described by Ohashi et al., U.S. Pat. No. 4,985,585. The compounds were obtained in laboratory scale amounts by silica-gel column chromatography of the crude product mixtures. The solvent was evaporated to give either a pale yellow oil or colorless crystals and no deliberate effort was made to control crystal morphology.

We have observed that 4-[6-acetyl-3-[3-(4-acetyl-3-hydroxy-2-propylphenylthio)propoxy]-2-propylphenoxy]butyric acid (1), which is Example 33 in Ohashi et al., is orally active for treatment of asthma and allergic diseases and that the solid compound can crystallize into several distinct polymorphs when prepared in bulk. It has been discovered that the crystallization conditions, particularly temperature, is critically important for preparing the different polymorphs.

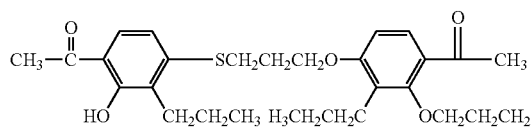

We have also found that the solubility and the bioavailability of one of these polymorphs, identified as orthorhombic crystals (Form V in Table 1, and Form A in FIG. 6), is superior to the other polymorphs and thus form A offers improved solid formulations.

SUMMARY OF THE INVENTION

The present invention provides a pharmaceutical composition comprising a compound of formula (1) in a selected crystalline form:

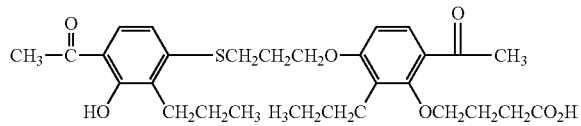

together with a pharmaceutically acceptable carrier or excipient, wherein the selected crystalline form is composed of polymorphic form A, substantially free of undesired polymorphs. By "substantially free" is meant that little or no undesired polymorphs are detectable by powder X-ray diffractometry (PXRD). Typically, the polymorphic purity is greater than 90% (defined by peak heights in the powder x-ray diffraction trace). Preferably, the desired crystalline form of the invention is at least about 95% of the polymorphic form A (FIG. 6) as measured by relative peak heights in the region of 9° 2-theta.

The present invention also provides a process for obtaining form A of the compound of formula (1) in at least about 90% purity with respect to other polymorphs. An exemplary crystallization process includes the steps of dissolving compound (1) in 5 to 10 parts by weight of warm ethanol and 1–10 parts of water, agitating the resulting suspension at 20–25° C. for 15–60 minutes and then cooling to 5–10° C. for an additional period of 1–4 hours, adding 5–15 parts of water, agitating the mixture at 5–10° C. for an additional 1–4 hours, and isolating crystals of compound (1) containing at least about 90% by weight of form A (FIG. 6).

Accordingly, a method for crystallizing the compound of formula (1) is provided, which method comprises:

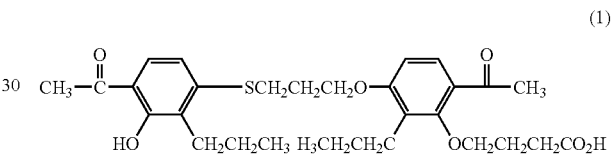

dissolving compound (1) in 5 to 10 parts by weight of ethanol and 1–10 parts of water, agitating the resulting suspension at 20–25° C. for 15–60 minutes and then cooling to 5–10° C. for an additional period of 1–4 hours, adding to this suspension 5–15 parts of water and agitating the mixture at 5–10° C. for an additional 1–4 hours, isolating crystals of compound (1) in polymorphic Form A, substantially free of other polymorphic forms. In a preferred method of the invention the isolated crystals of compound (1) contain at least about 90% of polymorphic Form A with respect to other polymorphic forms. The isolated crystals of compound (1) in a preferred embodiment exhibit a PXRD pattern substantially as shown for polymorphic Form A in FIG. 6. Moreover, the isolated crystals of compound (1) are at least about 90% polymorphic Form A, as defined by PXRD peak heights around 90° 2-theta. The desired, i.e., in a preferred embodiment, isolated crystals of compound (1) have a substantially orthorhombic crystal structure.

Yet another method of the invention, the crystallization of a compound of formula (1) is effected by steps comprising:

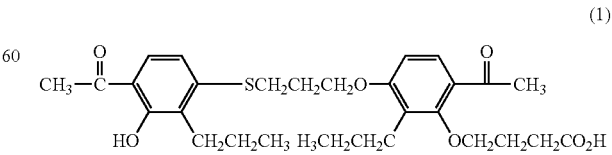

dissolving said compound in 5 to 7 parts by weight of ethanol at 30–40° C. and adding 1–2 parts of water, cooling the mixture to 10–15° C. over 2–3 hours and then cooling to 5–10° C. for an additional period of 1–4 hours, adding to this suspension 5–15 parts of water and agitating the mixture at 5–10° C. for an additional 1–4 hours, and isolating crystals of compound (1) in polymorphic Form A, which is substantially free of other polymorphic forms. Once more, in a preferred method, the isolated crystals of compound (1) exhibit at least about 90% of polymorphic Form A with respect to other polymorphs. Preferably, the isolated crystals of compound (1) exhibit a PXRD pattern substantially as shown for polymorphic Form A in FIG. 6. Also, preferred isolated crystals of compound (1) are at least about 90% polymorphic Form A, as defined by PXRD peak heights around 9° 2-theta. More preferably, the isolated crystals of compound (1) obtained by the instant method have a substantially orthorhombic crystal structure.

DETAILED DESCRIPTION OF THE INVENTION

Figure 1:
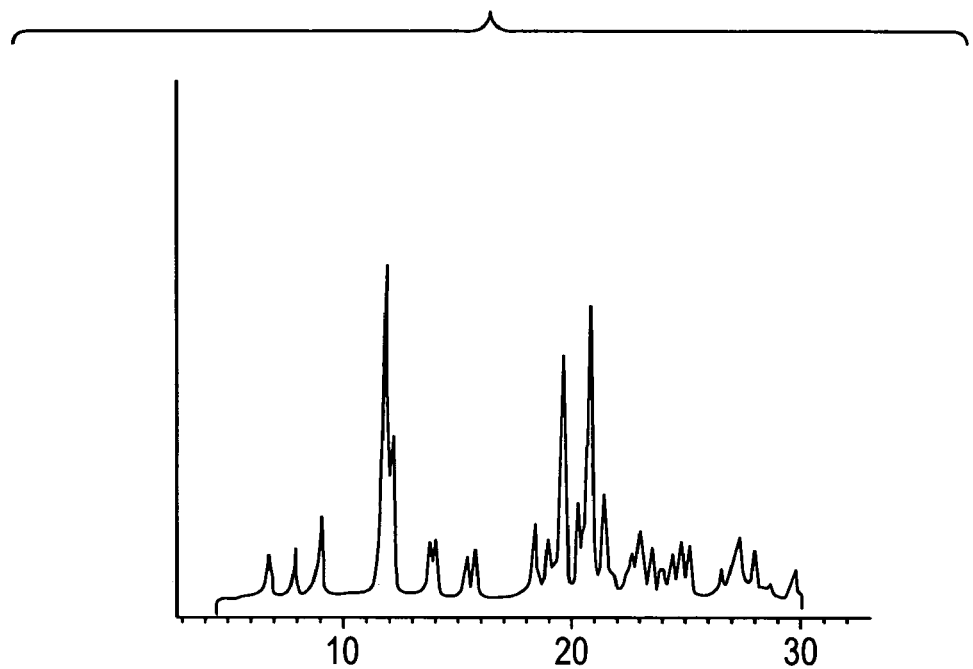
FIG. 1 Powder X-ray Diffraction Pattern and DSC Chart of Form I
FIG. 1a DSC Chart of Form I
FIG. 2 Powder X-ray Diffraction Pattern and DSC Chart of Form II
FIG. 3 Powder X-ray Diffraction Pattern and DSC Chart of Form III
FIG. 4 Powder X-ray Diffraction Pattern and DSC Chart of Form IV
FIG. 5 Powder X-ray Diffraction Pattern and DSC Chart of Form V
FIG. 6 X-ray diffraction patterns of three polymorphs.
Figure 1:
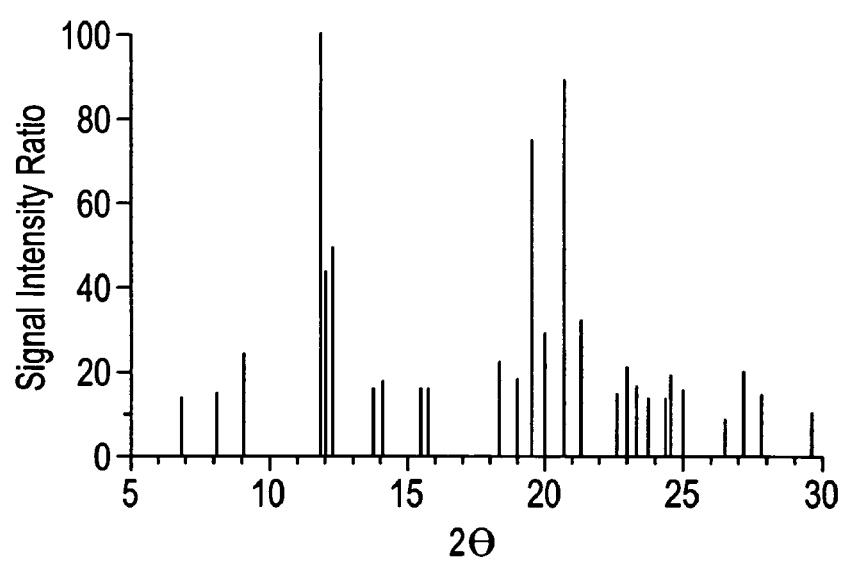
Figure 1A:
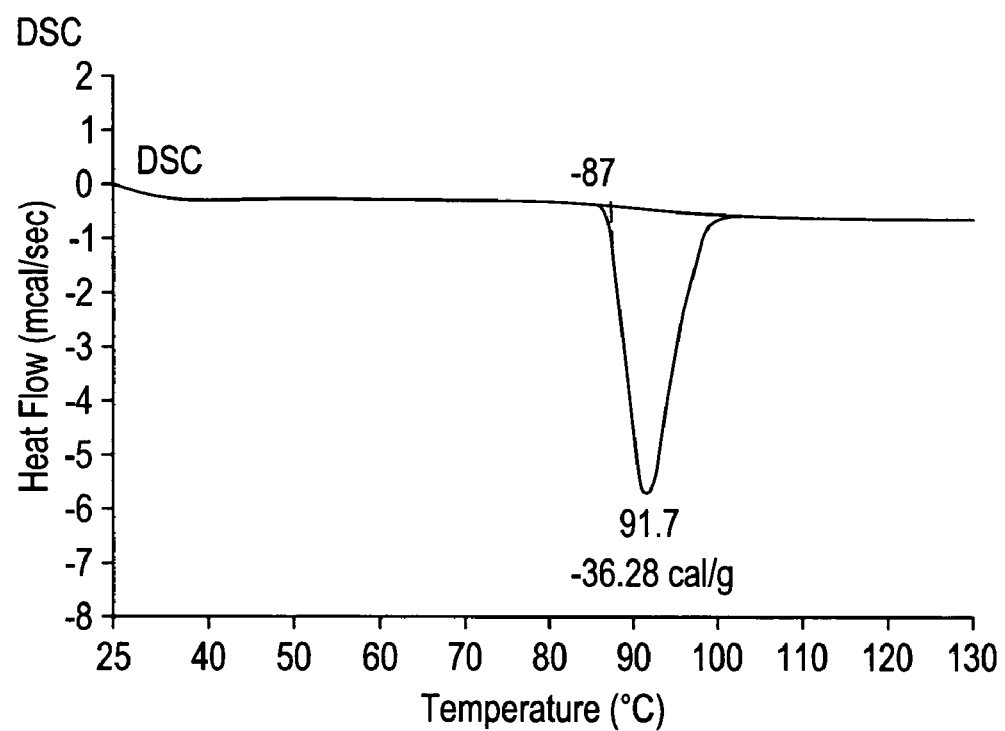
Figure 2:
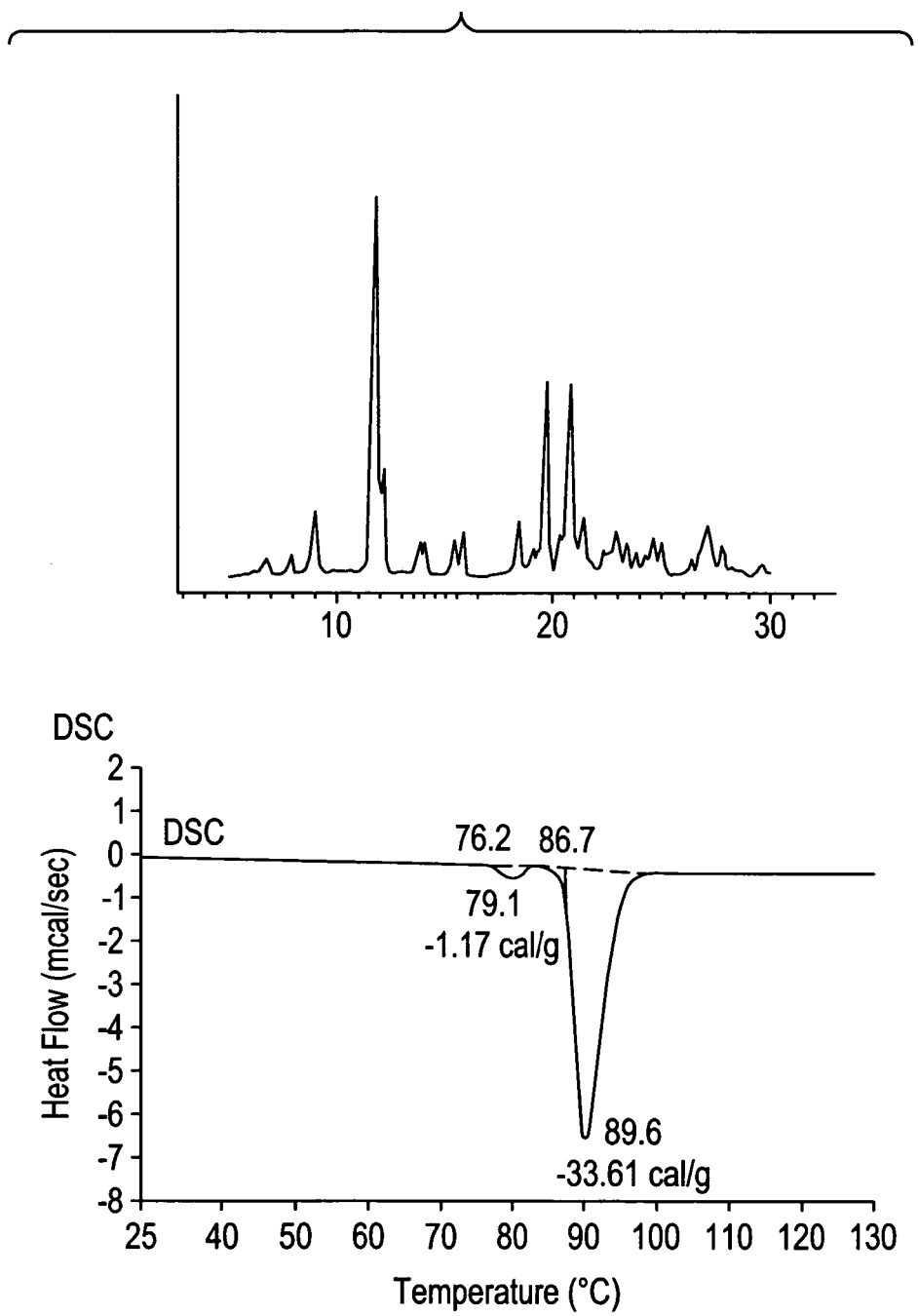
Figure 3:
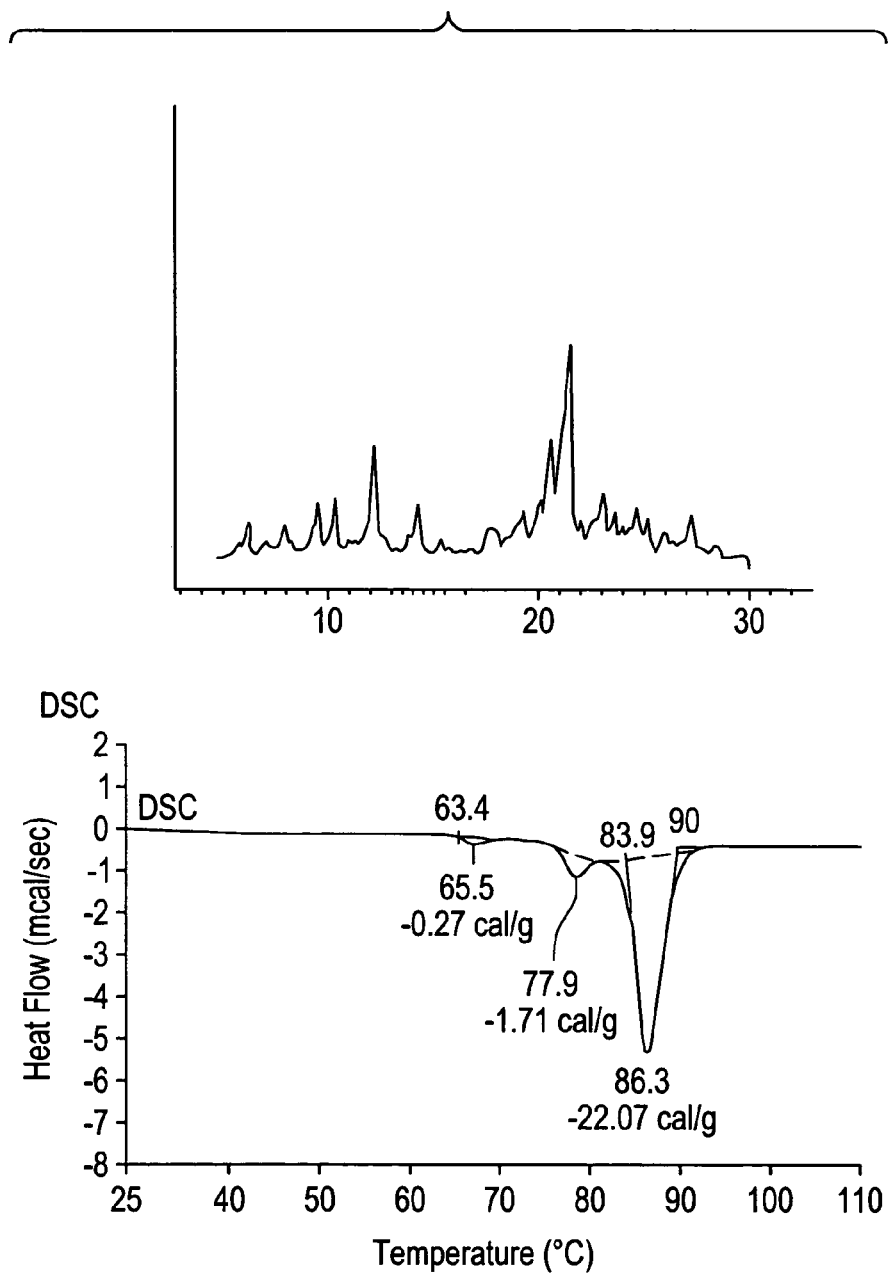
Figure 4:
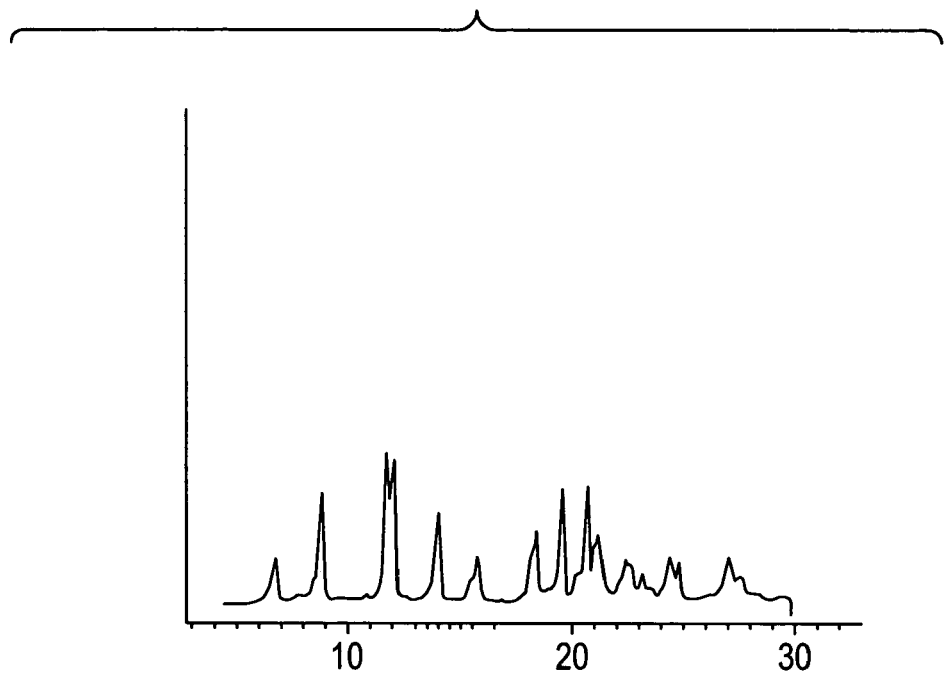
Figure 4:
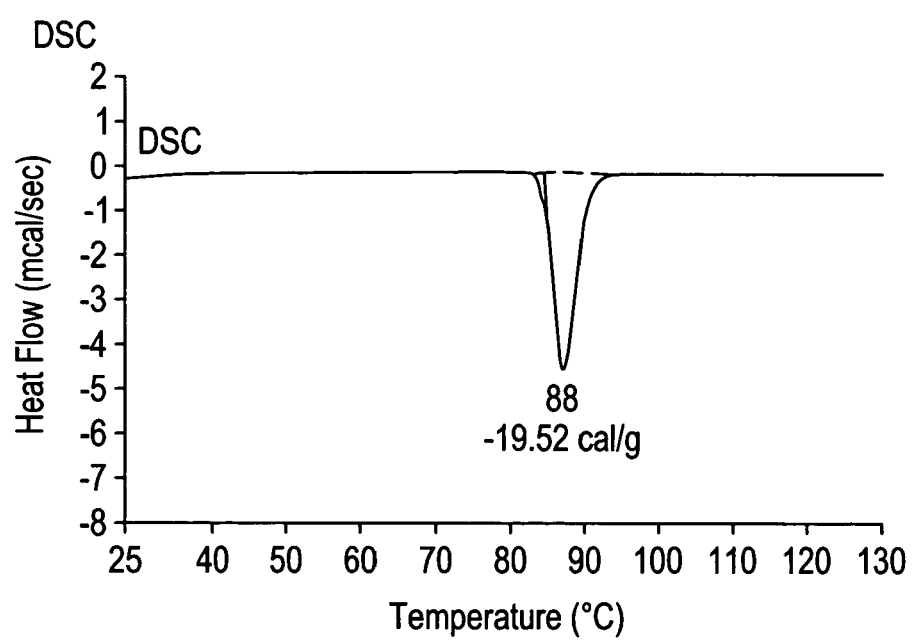

Ester (4) can be synthesized by reacting a phenol of formula (2):

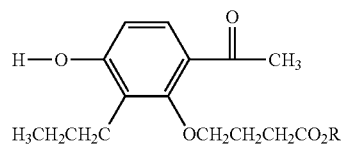

2 wherein R is an acid protecting group, such as methyl or ethyl, with the bromo compound of formula (3):

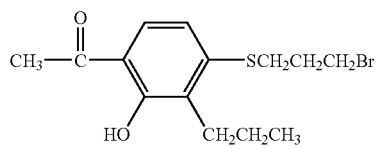

3 in an organic solvent, for example acetone, methylethylketone, diethylketone or dimethylformamide. The reaction may be conducted from below room temperature up to the reflux temperature of the solvent, in the presence of an inorganic base, e.g., potassium carbonate or sodium carbonate. The addition of potassium iodide is also recommended. Analogues of compound (3) having alternative leaving groups, such as chloro and tosylate, may be used to effect the coupling reaction.

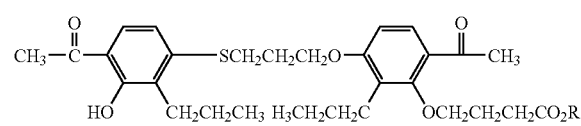

4

Removal of the acid protecting group by alkaline ester hydrolysis and extractive work-up gives compound (1) as a white solid.

Recrystallization of the white solid to give essentially pure form A crystals (FIG. 6), (e.g., 90% or more, preferably at least 95%) can be accomplished by dissolving compound (1) in 5 to 10 parts by weight of ethanol at 25–40° C. to give a yellow to orange solution. The ethanol solution is charged with 1–10 parts of water and agitated at 20–25° C. for about 15–60 minutes and then at 5–10° C. for an additional period of 1–4 hours, preferably 2.0–3.0 hours, resulting in an off-white suspension.

To this suspension is added 5–15 parts of water and the mixture is agitated at 5–10° C. for an additional 1–4 hours, preferably 1.5–2.0 hours. A solid, white to off-white product is isolated by vacuum filtration and the filter cake is washed with water and dried in a vacuum at 25–40° C. for 12–24 hours.

Other recrystallization conditions are also able to produce form A, such as dissolving compound (1) in a lower alcohol (isopropanol), and cooling the solution form crystals.

Therapeutic Formulations

Pharmaceutical compositions containing the orthorhombic form of compound (1) may be formulated for oral administration with inert excipients, such as a starch binder excipient, alone or in combination with microcrystalline cellulose and a suitable lubricant. Other suitable excipients include polyvinylpyrrolidinone, gelatin, hydroxy cellulose, acacia, polyethylene glycol, mannitol, sodium chloride, sodium citrate or any other excipient known to those of skill in the art of pharmaceutical compositions.

Excipients in tablets are generally classified according to their function, such as diluents (also called bulking agents and fillers), binders which hold the ingredients together in the compressed tablet, disintegrants which help facilitate the break-up of the tablet when placed in a fluid environment to release the active ingredient, and lubricants to improve the release of the compressed tablet from the die and punches. In addition, tablets may contain other substances intended to improve the tabletting process, such as flow additives, flavors, sweeteners and anti-oxidants Tabletting and some capsule filling operations are based on the ability of certain powders to bind under compression. Compressed tablets may be prepared by wet granulation, dry granulation, or direct compression. The wet granulation process includes mixing the components in powder form, preparing the granulating binder solution, thoroughly mixing the components with the granulating binder solution to form a dough, coarse screening the mass through a sieve, drying, grinding, adding the lubricant and compressing the tablets from the resulting mixture.

A preferred tablet formulation is a wet granulation containing polymorphic form A of compound (1) lactose regular, microcrystalline cellulose 101, crosscarmellose, magnesium stearate and purified water, coated with Opadry II white. The tablets should weigh from 100 mg to 1000 mg, preferably 250 mg to 500 mg.

Dry granulation involves the steps of mixing the powder components, compressing the mixture into hard slugs, grinding the slugs into desired particle size, screening, adding other excipients if necessary, and compressing the mixture into tablets. The most economical tabletting method, direct compression, requires only two steps, mixing the dry components and compressing the mixture into tablets.

Suitable direct compression binders include microcrystalline cellulose, compressible sugars, certain calcium salts, lactose and dextrose. Of these, microcrystalline cellulose is preferred. That excipient also displays good disintegration properties. Other good binders include calcium phosphates and compressible sugars. Calcium salt binders generally require the use of disintegrants. Mannitol and sorbitol have certain taste advantages, but they lack binding properties and require a disintegrant.

The tablets typically exhibit a tablet hardness of greater than 2 kilopond (kp)/cm.sup.2, more preferably a tablet hardness of greater than 5, most preferably about 10 to about 20 kp/cm.sup.2 and a disintegration time of less than 30 minutes, more preferably less than 15 minutes as measured utilizing the standard USP disintegration test in water.

The polymorphic form A of compound (1) may also be formulated in capsules. Solid carriers include starch, lactose, calcium sulfate, di-hydrate, teffa alba, magnesium stearate or stearic acid, talc, pectin, acacia, agar or gelatin. The carrier may also include a sustained release material such as glycerol monostearate or glycerol di-stearate, alone or with a wax. The amount of solid carrier varies but, preferably, will be between about 20 mg to about 1 gram per dosage unit.

Encapsulation can be done in any suitable manner, typically by use of a polymer coating used for microencapsulation, enteric coatings, multiple coatings, and the like. The polymer coating may resist disintegration upon contact with the saliva but instantly release the compound upon contact with gastric juice in the stomach, in order to control the taste of the composition. Alternatively, the polymer coating may be one that resists rapid disintegration in the presence of gastric juice. Suitable coating polymers include biodegradable polymers such as polylactic acid, polygycolic acid, copolymers of lactic and glycolic acid, polyorthoesters, and polyanhydrides thereof. The compound also can be encapsulated by a polymer coating such as a polysaccharide (e.g., methyl or ethyl cellulose) or within a liposomal delivery system. Suitable methods of preparing compositions containing microencapsulated active ingredients are described, for example, in U.S. Pat. Nos. 4,462,982, 4,710,384, 5,178,878, and 5,709,886. Preferably, the microencapsulated compounds have a mean particle size of about 50 microns to about 120 microns (e.g., about 70 microns to about 100 microns).

Typical doses of compound (1) in tablets and capsules are from about 1.0 mg/kg to about 100 mg/kg. Administration intervals vary with the patient's age, weight and general condition. In general, the drug is administer from one to four times daily.

EXAMPLES

In general, tablets are formed utilizing a carrier such as modified starch, alone or in combination with 10% by weight of carboxymethyl cellulose (Avicel). The formulations are compressed at from 1,000 to 3,000 pounds pressure in the tablet-forming process. The tablets preferably exhibit an average hardness of about 1.5 to 8.0 kp/cm.sup.2, preferably 5.0 to 7.5 kp/cm2. Disintegration time varies from about 30 seconds to about 15 or 20 minutes. The following examples give specific embodiments of the invention but should not be construed as limiting its scope.

Example 1

Synthesis of ethyl 4-[6-acetyl-3-[3-(4-acetyl-3-hydroxy-2-propylphenylthio)-propoxy]-2-propyl phenoxy]butyrate To a stirred mixture of ethyl 4-(6-acetyl-3-hydroxy-2-propylphenoxy)butyrate (1.6 g), potassium iodide (0.5 g) and potassium carbonate (1.45 g) in acetone (30 ml) was added drop wise a solution of 4-(3-bromopropylthio)-2-hydroxy-3-propylphenyl-ethanone (1.9 g) in acetone (10 ml) with heating to reflux. After refluxing six hours the mixture was cooled to room temperature and inorganic materials were separated by filtration. The filtrate was concentrated and the residue was separated and purified by silica-gel column chromatography (eluting with benzene:ethyl acetate=9:1) to give the title compound as crude crystals (2.1 g, 72.4%) which were recrystallized from ethanol to give colorless crystals, mp 65–66° C.

Example 2

Synthesis of 4-[6-acetyl-3-[3-(4-acetyl-3-hydroxy-2-propylphenylthio)propoxy]-2-propylphenoxy]butyric acid To a mixture of ethyl 4-[6-acetyl-3-[3-(4-acetyl-3-hydroxy -2-propylphenylthio)propoxy]-2-propylphenoxy]butyrate (2.1 g) in ethanol (10 ml) was added a solution of sodium hydroxide (0.26 g) dissolved into water (10 ml). After heating on a hot water bath for 5 minutes, the mixture was cooled by adding ice-water and was made acidic by addition of hydrochloric acid, followed by extraction with ethyl acetate. The organic layer was washed with water, dried over sodium sulfate and concentrated. The resultant residue was separated and purified by silica-gel column chromatography (eluting with ethanol:methylene chloride=3:100) to give the title compound (1.3 g, 65.2%) as colorless crystals, mp 79–81° C.

Example 3

Crystalline Polymorphism

After re-crystallization with individual solvents, compound (1) was subjected to powder X-ray diffractometry, thermal analysis and determination of solubility in ether; thus an exploratory evaluation of the crystalline polymorphism was made. The results demonstrate that compound (1) is present in 5 different crystalline polymorphs.

FIGS. 1–5 show the powder X-ray diffraction patterns and DSC for metastable crystal types I through V. Table 1 shows the preparatory procedures for types I through V and their solubility in ether.

TABLE 1

Preparation of Crystalline Polymorphs and Their Solubilities in Ether

| Crystal form | Preparatory procedures | Solubility (mg/mL) |
|---|---|---|
| I | After compound (1) was heated and dissolved in a 4-fold quantity of isopropyl ether, the resultant solution was allowed to cool at room temperature (crystallization took place in the vicinity of 40° C.). Alternatively, after the compound was heated and dissolved in a 5-fold quantity of acetonitrile, the resultant solution was maintained at 40° C. in an incubator. | 36.7 |
| II | After compound (1) was heated and dissolved in a 10-fold quantity of acetonitrile, the resultant solution was cooled and agitated in an ice water bath. | 40.5 |
| III | After compound (1) was heated and dissolved in a 10-fold quantity of acetonitrile, the resultant solution was maintained at 25° C. in an incubator. | 35.3 |
| IV | After compound (1) was heated and dissolved in a 5-fold quantity of ethanol, a 2.5-fold quantity of water was added thereto while hot, which was then allowed to cool at room temperature. | 45.8 |
| V | After compound (1) was heated and dissolved in a 5-fold quantity of ethanol, the resultant was cooled and agitated in an ice water bath, and a 2.5-fold quantity of water was added thereto while cold. Alternatively, compound (1) was heated and dissolved in a 3.5-fold quantity of isopropanol and the resulting solution was maintained at 0° C. in a refrigerator. | 47.6 |

Table 1 shows that the crystallization temperature was critically important in preparing the various crystalline polymorphs. When the bulk ingredient is prepared, crystallization takes place on a large scale and failure in controlling the exact temperature can result in a mixture of stable and metastable crystals, giving a larger variance in the physicochemical properties and bioavailability among production lots, against which precautions should be taken.

Example 4

Bulk Crystallization Procedure for Obtaining Orthorhombic Polymorph, Crystal Type V (Form A)

Off-white solid compound (1) 34 g was dissolved in 204 mL (6 parts wrt mass of dry filter cake) of ethanol (40° C.) giving a yellow to orange solution. With moderate agitation, the ethanol solution was charged with 43 mL (1.3 parts) of water. The reaction mixture was cooled to 20–25° C. and agitated at 20–25° C. for about 15 minutes and then at 10–15° C. for an additional period of 1–2 hours, appearing as an off-white suspension.

To the resulting suspension was then charged 364 mL (10.7 parts) of water and the mixture was agitated at 5–10° C. for an additional 1–2 hours. A solid, white to off-white product was isolated by vacuum filtration. The filter cake was washed with 2×30 mL of water. The off white solid was dried in a vacuum at 35–40° C. for 24 hours.

Example 5

Solubility data of compound (1) in ethanol/water (2:1)

| temperature | desired polymorphic form V (form A) | undesired monoclinic polymorph |
|---|---|---|
| 22° C. | 6.7 g/L | 3.4 g/L |
| 30° C. | 15.7 g/L | 6.1 g/L |
| 40° C. | 46 g/L | 17.2 g/L |

Samples of compound (1) (5 g) were suspended in ethanol/water (2:1, 100 mL) and stirred for one hour at temperatures of 22° C., 30° C., and 40° C., respectively. The suspensions were filtered and the solids dried in a vacuum oven at room temperature overnight to give the insoluble material. The solubilities were calculated by subtractive means based on recovered material.

Example 6

In general wet granulation tablets were prepared with a binding solution comprised of an aqueous solution of hydroxypropylcellulose. Granulation was performed with a high shear granulator, the resultant wet mass was fluid bed dried, milled, blended with extragranular excipients to aid disintegration, flow and compressibility, and subsequently tabletted on a tablet press. These core tablets were film coated to standardize appearance and to improve compliance (i.e. ease of swallowing). Excipients included, but were not limited to croscarmellose sodium, magnesium stearate, hydroxypropylcelluse, hydroxypropylmethylcellulose, lactose, glyceryl behenate, polyvinylpyrrolidine, mannitol,titanium dioxide and microcrystalline cellulose.

Example 7

In general, the dry granulation formulation was formed by dry blending (in a tumble blender or high shear mixer) a portion of the binding, disintegration and lubrication powders. This dry powder blend was formed into granules through the use of a roller compactor equipped with an oscillating (shear) granulator. The ss mesh screen, gap width, gap force, roller speed and granulator speeds were defined to optimize the formulation physical parameters as apparent to those skilled in the art of pharmaceutical processing. Excipients included, but were not limited to croscarmellose sodium, magnesium stearate, hydroxypropylcelluse, hydroxypropylmethylcellulose, lactose, glyceryl behenate, polyvinylpyrrolidine, mannitol, titanium dioxide and microcrystalline cellulose.

Example 8

Specific Formulation for Dry Granulation

TABLE 3.4.1

Proposed initial formulation compositions for dry granulation prototyping

| No. | Ingredient | Prototype 1 (mg/tablet) | Prototype 2 (mg/tablet) |
|---|---|---|---|
| 1 | Compound (1), Type V (Form A) | 250 | 250 |
| 2 | Lactose regular/fast flow | 7.5 | — |
| 3 | Microcrystalline cellulose PH101 | 31 | 31 |
| 4 | Croscarmellose sodium | 20 | 20 |
| 5 | Hydroxypropylcellulose | 80 | — |
| 6 | Magnesium stearate | 2.0 | — |
| 7 | Hydroxypropylmethylcellulose 2910 | 8.0 | — |
| 8 | Titanium Dioxide | 1.0 | — |
| 9 | Carnauba wax | 0.5 | 0.5 |
| 10 | Polyvinylpyrrolidone | — | 85 |
| 11 | Mannitol | — | 3.5 |
| 12 | Glyceryl behenate | — | 2.0 |
| 13 | Opadry II (white) | — | 8.0 |
|  | Total | 400 mg | 400 mg |

Figure 7:
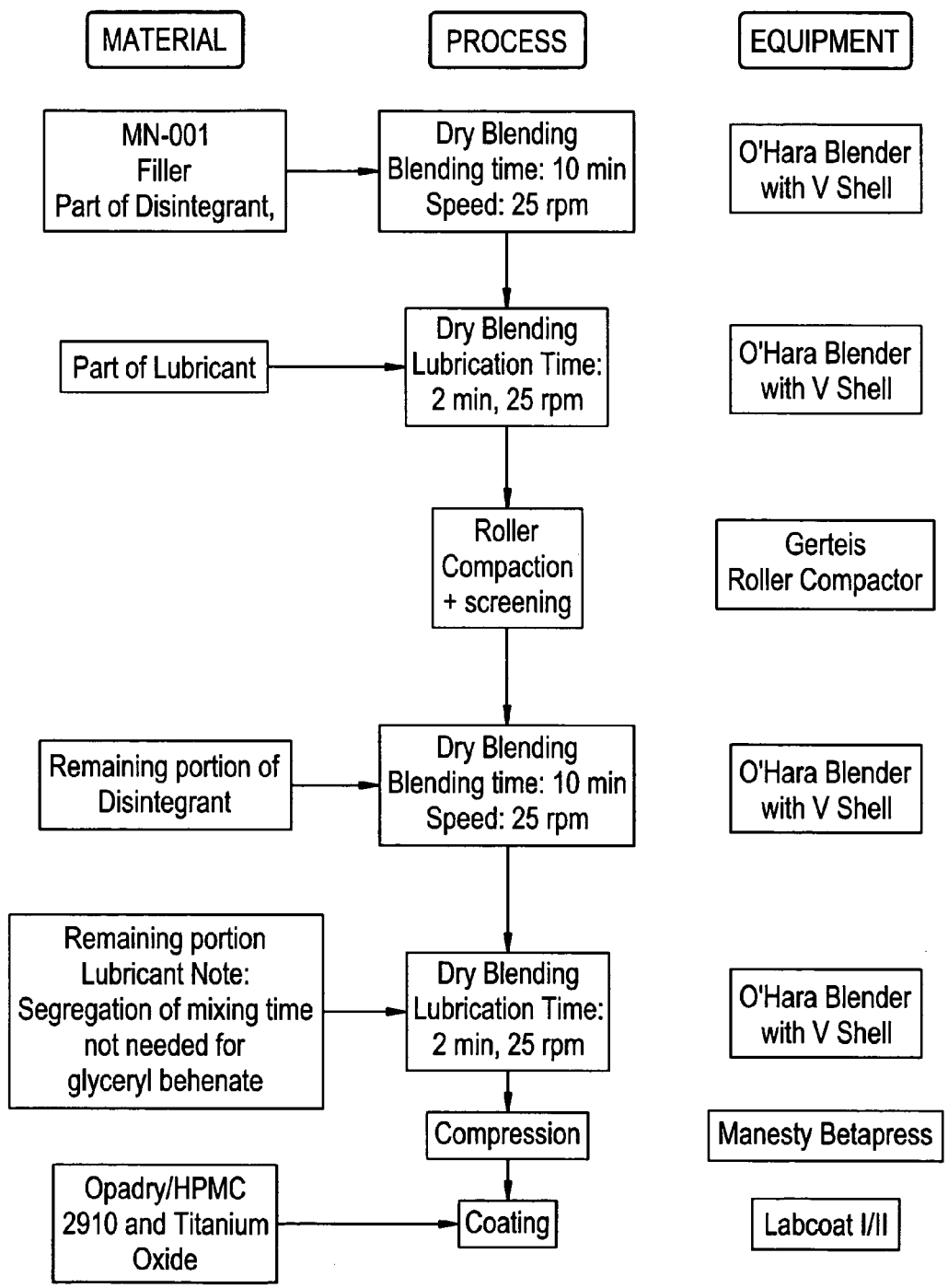
FIG. 7 Schematic process for dry granulation
FIG. 8 Schematic process for wet granulation

The dry granulation process is given in the chart in FIG. 7.

Example 9

Specific Formulation for Dry Granulation

TABLE 3.4.2

Proposed initial formulation compositions for wet granulation prototyping

| No. | Ingredient | Prototype 3 (mg/tablet) | Prototype 4 (mg/tablet) |
|---|---|---|---|
| 1 | Compound (1), Type V (Form A) | 250 | 250 |
| 2 | Lactose regular/fast flow | 7.5 | — |
| 3 | Microcrystalline cellulose PH101 | 32 | 32 |
| 4 | Croscarmellose sodium | 25 | 25 |
| 5 | Hydroxypropylcellulose | 25 | — |
| 6 | Magnesium stearate | 2.0 | — |
| 7 | Hydroxypropylmethylcellulose 2910 | 7.0 | — |
| 8 | Titanium Dioxide | 1.0 | — |
| 9 | Carnauba wax | 0.5 | 0.5 |
| 10 | Polyvinylpyrrolidone | — | 30 |
| 11 | Mannitol | — | 3.5 |
| 12 | Glyceryl behenate | — | 2.0 |
| 13 | Opadry II (white) | — | 7.0 |
|  | Total | 350 mg | 350 mg |

Figure 8:
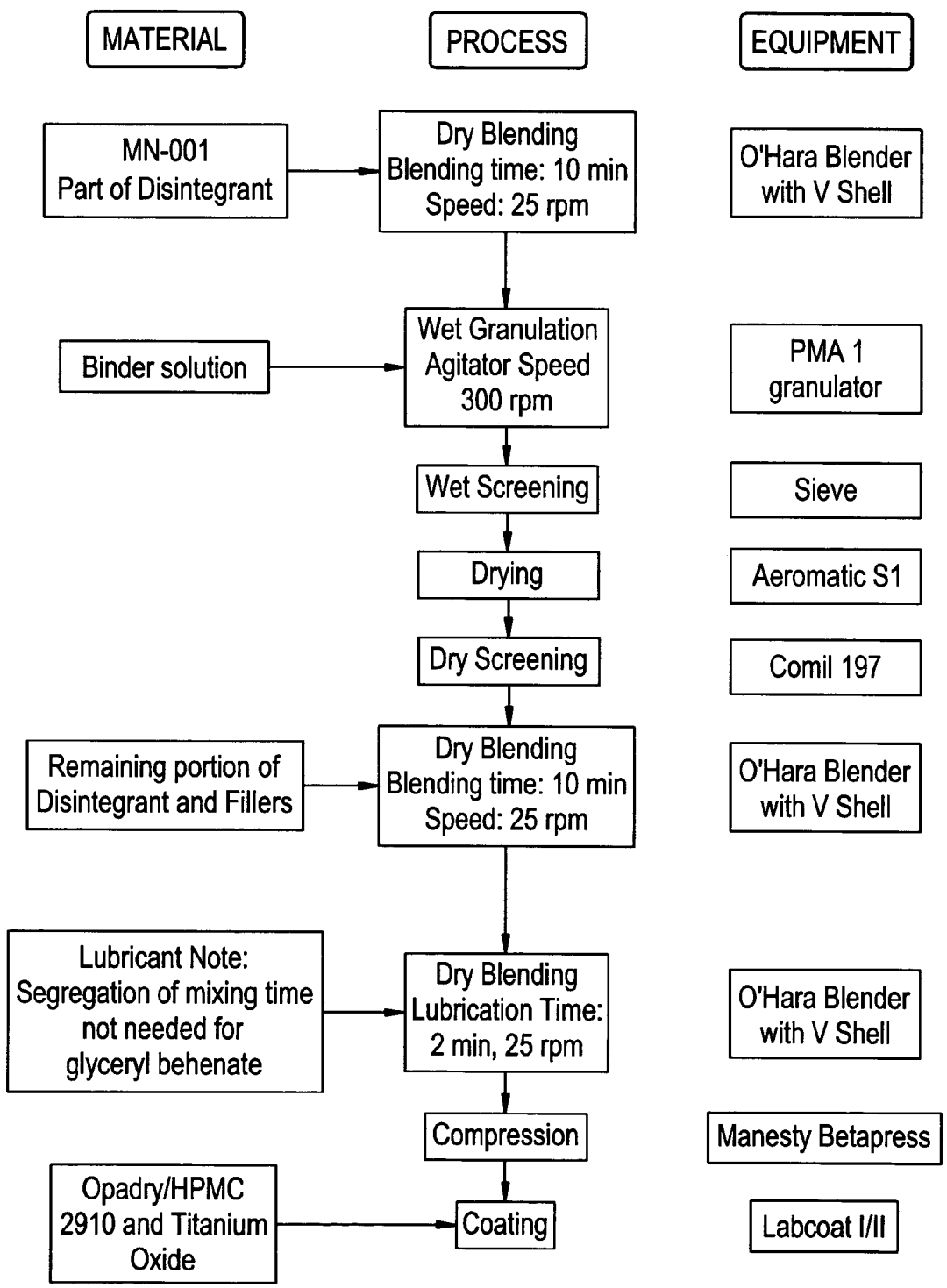

The wet granulation process is given in the chart in FIG. 8.

The preferred embodiments of the invention have been described above in detail. Various modifications and improvements thereto will become readily apparent to those skilled in the art. The foregoing examples are intended to be non-limiting and exemplary of the invention described in the foregoing specification and claimed below.

Example 10

PXRD Analysis

The samples were prepared by a normal front packing technique and run on a Siemens D5000 Diffractometer System. A high-resolution Cu—Kα-source was used, operating at 50 kV/35 mA. The secondary beam was monochromatized by a Kevex solid state detector. The step scan mode was used for data collection within the range of 2.5°–35° (2-theta). The obtained data were processed by Diffrac Plus™ Software.

Figure 6:
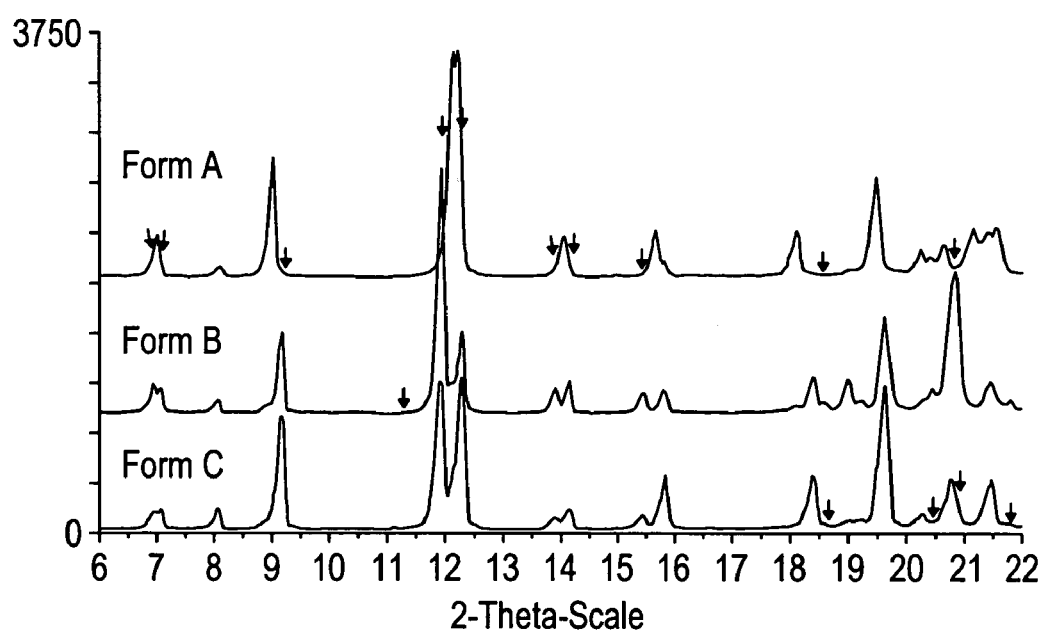

The parts of the diffraction patterns of three different polymorphs are shown in FIG. 6, determined as Form A (likely an orthorhombic structure, specified type V), Form B (I) and Form C (II) (both monoclinic lattices) are also shown.

As on can see the top pattern is quite different from the other two. The differences are clearly marked with arrows above the top trace. Most of the single peaks on the upper pattern became doublets on the other two. This strongly suggests a structural transition with lowering of the overall symmetry. In order to find out some criteria for better distinguishing of these polymorphous, an attempt for indexing the unknown lattices was performed. The results reveal an orthorhombic lattice (top trace, Form A) and a monoclinic one (middle trace, Form B). The bottom trace (Form C) has also a monoclinic lattice very similar to that one of Form B, but with some missing reflections (marked with arrows) that could result from some structural differences.

Figure 5:
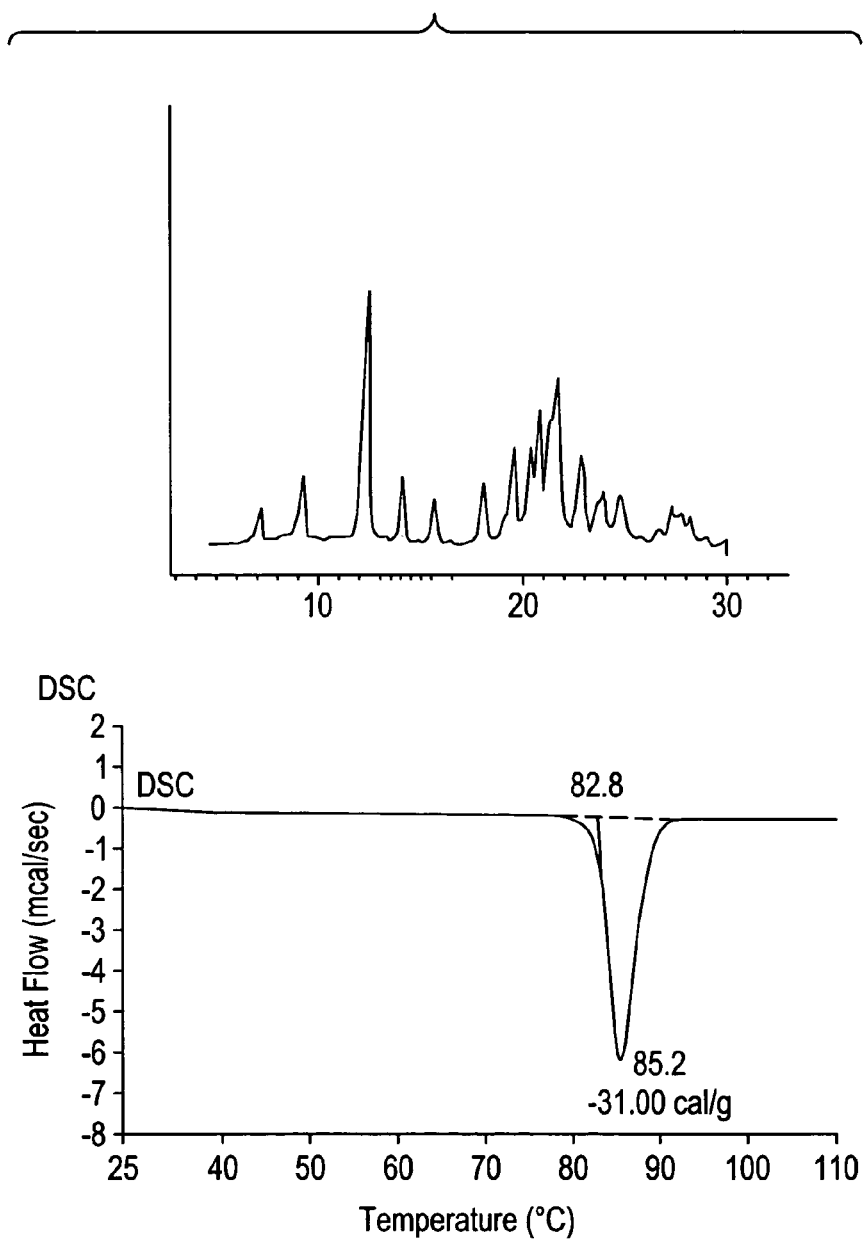

The structure of our Form A is very close to Form V in Table 1 and FIG. 5, although there are some differences at the range 19–25° 2-theta. On the other hand, the diffraction patterns for polymorphous Form I and Form II match well with Forms B and C, as they all apparently show the splitting of the main reflections due to reducing the overall symmetry from orthorhombic to monoclinic.

Because crystallographic characterizations of all five polymorphous described in Table 1 are difficult to reproduce, we will characterize the structural state of compound (1) in pharmaceutical samples only by means of its appearance as Form A, as defined by PXRD.

The invention claimed is:

1. A method of providing isolated orthorhombic crystalline 4-[6-acetyl-3-[3-(4-acetyl-3-hydroxy-2-propylphenylthio)propoxy]-2-propylphenoxy]butyric acid, which orthorhombic crystalline form (i) is substantially free of monoclinic crystalline forms as evidenced by powder x-ray diffraction (PXRD) analysis showing the absence of doublet peaks between about 11.5 and 16 (2-Theta scale), and (ii) exhibits at least twice the solubility of a monoclinic crystalline form at 30° C. in aqueous ethanol, comprising:

(a) dissolving 4-[6-acetyl-3-[3-(4-acetyl-3-hydroxy-2-propylphenylthio)propoxy]-2-propylphenoxy]butyric acid in 5 to 10 parts by weight of ethanol and 1 to 10 parts of water agitating the resulting suspension at 20–25° C. for 15–60 minutes and then cooling to 5–10° C. for an additional period of 1–4 hours;

(b) adding to this suspension 5 to 15 parts of water and agitating the mixture at 5–10° C. for an additional period of 1–4 hours; and (c) isolating orthorhombic crystals of 4-[6-acetyl-3-[3-(4-acetyl-3-hydroxy-2-propylphenylthio)propoxy]-2-propylphenoxy]butyric acid, which are substantially free of monoclinic crystalline forms.

2. A method of providing isolated orthorhombic crystalline 4-[6-acetyl-3-[3-(4-acetyl-3-hydroxy-2-propylphenylthio)propoxy]-2-propylphenoxy]butyric acid, which orthorhombic crystalline form (i) is substantially free of monoclinic crystalline forms as evidenced by powder x-ray diffraction (PXRD) analysis showing the absence of doublet peaks between about 11.5 and 16 (2-Theta scale), and (ii) exhibits at least twice the solubility of a monoclinic crystalline form at 30° C. in aqueous ethanol, comprising:

(a) dissolving 4-[6-acetyl-3-[3-(4-acetyl-3-hydroxy-2-propylphenylthio)propoxy]-2-propylphenoxy]butyric acid in 5 to 7 parts by weight of ethanol at 30–40° C. and adding 1–2 parts of water, cooling the mixture to 10–15° C. over 2–3 hours and then cooling to 5–10° C. for an additional period of 1–4 hours.

(b) adding to this suspension 5–15 parts of water and agitating the mixture at 5–10° C. for an additional period of 1–4 hours; and (c) isolating orthorhombic crystals of 4-[6-acetyl-3-[3-(4-acetyl-3-hydroxy-2-propylphenylthio)propoxy]-2-propylphenoxy]butyric acid, which are substantially free of monoclinic crystalline forms.

3. A method of isolating orthorhombic crystalline 4-[6-acetyl-3-[3-(4-acetyl-3hydroxy-2-propylphenylthio)propoxy]-2-propylphenoxy]butyric acid, which orthorhombic crystalline form is substantially free of monoclinic crystalline forms, comprsing:

(a) dissolving 4-[6-acetyl-3-[3-(4-acetyl-3-hydroxy-2-propylphenylthio)propoxy]-2-propylphenoxy]butyric acid in ethanol;

(b) adding water and cooling the resulting mixture first to about 10–15° C. and second to about 5–10° C., (c) adding more water and agitating the resulting mixture at about 5–10° C., and (d) isolating orthorhombic crystals of 4-[6-acetyl-3-[3-(4-acetyl-3-hydroxy-2-propylphenylthio)propoxy]-2-propylphenoxy]butyric acid, which are substantially free of monoclinic crystalline forms.

4. A method of recrystallizing 4-[6-acetyl-3-[3-(4-acetyl-3-hydroxy-2-propylphenylthio)propoxy]-2-propylphenoxy]butyric acid, comprising:

(a) dissolving 4-[6-acetyl-3-[3-(4-acetyl-3-hydroxy-2-propylphenylthio)propoxy]-2-propylphenoxy]butyric acid in 5 to 10 parts by weight of ethanol at about 25–40° C.;

(b) adding 1–10 parts of water and agitating at 20–25° C. for about 15–60 minutes;

c) cooling to about 5–10° C. for a period of 1–4 hours;

d) adding 5–15 parts of water and agitating at about 5–10° C. for a period of about 1–4 hours; and e) isolating orthorhombic crystals of 4-[6-acetyl-3-[3-(4-acetyl-3-hydroxy-2-propylphenylthio)propoxy]-2-propylphenoxy]butyric acid, which are substantially free of monoclinic crystalline forms.

5. The method of claim 4 in which the cooling of step (c) is carried out for a period of 2–3 hours.

6. The method of claim 4 in which the agitating step (d) is carried out for a period of 1.5–2 hours.

7. A method of recrystallizing 4-[6-acetyl-3-[3-(4-acetyl-3-hydroxy-2-propylphenylthio)propoxy]-2-propylphenoxy]butyric acid, comprising:

a) dissolving 4-[6-acetyl-3-[3-(4-acetyl-3-hydroxy-2-propylphenylthio)propoxy]-2-propylphenoxy]butyric acid in 5 to 10 parts by weight of ethanol at about 25–40° C.;

b) adding 1–10 parts of water;

c) agitating at 20–25° C. for about 15–60 minutes;

d) agitating at about 5–10° C. for a period of about 1–4 hours;

e) adding 5–15 parts of water;

f) agitating at about 5–10° C. for a period of about 1–4 hours; and g) isolating orthorhombic crystals of 4-[6-acetyl-3-[3-(4-acetyl-3-hydroxy-2-propylphenylthio)propoxy]-2-propylphenoxy]butyric acid, which are substantially free of monoclinic crystalline forms.

8. A method of preparing a pharmaceutically acceptable tablet or capsule containing isolated orthorhombic crystalline 4-[6-acetyl-3-[3-(4-acetyl-3-hydroxy-2-propylphenylthio)propoxy]-2-propylphenoxy]butyric acid, which orthorhombic crystalline form is substantially free of monoclinic crystalline forms, comprising:

a) combining pharmaceutically acceptable components of a tablet or capsule, including isolated orthorhombic crystalline 4-[6-acetyl-3-[3-(4-acetyl-3-hydroxy-2-propylphenylthio)propoxy]-2-propylphenoxy]butyric acid, which orthorhombic crystalline form is substantially free of monoclinic crystalline forms, to provide a mixture; and b) compressing the mixture into a tablet of filling a capsule with the mixture.

9. The method of claim 8 which further comprises a wet granulation step or a dry granulation step prior to the compression step in the case of a tablet.

* * * * *